United States Patent [19]

Pisano

[11] Patent Number: 5,682,616
[45] Date of Patent: Nov. 4, 1997

[54] HOSIERY HAVING A PROTECTIVE SLEEVE FOR PREVENTING DEBRIS-INTRUSION

[76] Inventor: Mark A. Pisano, 214 Linden Ave., Pittsburgh, Pa. 15238

[21] Appl. No.: 554,525

[22] Filed: Nov. 7, 1995

[51] Int. Cl.⁶ ........................................................ A41B 11/00
[52] U.S. Cl. ............................ 2/239; 2/16; 2/22; 2/59
[58] Field of Search ............................ 2/239, 240, 242, 2/22, 1, 16, 46, 59, 61, 2; 602/3–6, 20, 21, 23

[56] References Cited

U.S. PATENT DOCUMENTS

| | | | |
|---|---|---|---|
| 5,020,164 | 6/1991 | Edwards | 2/239 |
| 5,054,129 | 10/1991 | Baehr | 2/239 |
| 5,157,791 | 10/1992 | Woodson et al. | 2/239 |
| 5,415,622 | 5/1995 | Kelley | 602/5 |

FOREIGN PATENT DOCUMENTS

| | | | |
|---|---|---|---|
| 722958 | 3/1932 | France | 2/239 |
| 982991 | 6/1951 | France | 2/239 |
| 2457645 | 1/1981 | France | 2/239 |
| 484752 | 10/1929 | Germany | 2/239 |
| 24755 | 7/1914 | Norway | 2/239 |

OTHER PUBLICATIONS

Sears Wish Book Catalog, p. 165, Items 1–6; Winter 1980

*Primary Examiner*—C. D. Crowder
*Assistant Examiner*—Gloria Hale
*Attorney, Agent, or Firm*—Webb Ziesenheim Bruening Logsdon Orkin & Hanson, P.C.

[57] ABSTRACT

The present invention discloses debris-resistant or intrusion-resistant hosiery, particularly a sock. The sock generally includes a flexible main sleeve member with an opening at one end thereof, a hollow body portion, and a resilient gripping member substantially surrounding the opening and adapted to attach the sock to the user. The sock includes a flexible, protective sleeve member coupled to the hollow body portion with the protective sleeve member including an opening at one end and elastic attaching members surrounding the opening and adapted to secure the protective sleeve member to footwear or the like. The footwear protecting sock of the present invention has particular applications for construction boots, snow boots and casts.

6 Claims, 2 Drawing Sheets

HOSIERY HAVING A PROTECTIVE SLEEVE FOR PREVENTING DEBRIS-INTRUSION

BACKGROUND OF THE INVENTION

1. Field of the Invention

The present invention relates to protective hosiery and, more specifically, the present invention relates to a footwear protecting sock for preventing the intrusion of material into said footwear.

2. Background of the Invention

There is a need to mitigate the intrusion of extraneous material into footwear. For example, in the construction industry, work boots are commonly used due to the relatively harsh environment. A particular problem with work boots is the intrusion of water, snow or debris such as dirt and pebbles into the interior of the boot, which is generally uncomfortable to the wearer.

Although the nature of the construction industry illustates this particular problem, the problem is not limited to work boots in the construction industry. Snow boots and, in particular, children's snow boots are also of concern. Snow entering through the open top portion of a user's snow boot makes the user quite uncomfortable. Additionally, with small children, the risk of frostbite becomes an even more significant concern.

In a similar fashion to the footwear described above, the intrusion of debris or other material into a hardened cast of the type used to set bone fractures can make the patient particularly uncomfortable. This problem is heightened with a cast in that the user cannot readily remove the cast to remove the associated debris. Furthermore, the problem becomes more apparent as the cast remains in place. With a hardened cast in place, the associated muscle often atrophies, shrinking in size. The atrophied muscle will increase the gap between the cast as originally placed in position and the user's skin, increasing the likelihood of debris and other material entering said gap and causing irritation or infection.

It is an object of the present invention to provide a protective member to prevent the above-described intrusion of foreign material. It is a further object of the present invention to provide such a protective member which is quickly and easily utilized and which is simple and economical to manufacture.

SUMMARY OF THE INVENTION

The above-identified objects of the present invention are satisfied by providing protective hosiery which includes a flexible main sleeve member and a flexible, protective sleeve member coupled thereto. The flexible main sleeve member has a hollow body portion, an opening at a first end thereof and an attachment mechanism surrounding the opening. The flexible, protective sleeve member is coupled to the hollow body portion of the main sleeve member with the protective sleeve member having an opening at a first end thereof and an attachment mechanism surrounding the opening.

In one embodiment of the present invention, the protective hosiery is in the form of a footwear-protecting sock. The flexible main sleeve member of the protecting sock includes the opening at a first end thereof which is adapted to receive the user's foot and a portion of the leg therethrough. The hollow body portion includes a toe-receiving portion, heel-receiving portion and a leg-receiving portion. Elastic gripping members form the attachment mechanism of the main sleeve member and substantially surround the opening of the main sleeve member and are adapted to secure the sock to the leg of the user. The flexible, protective sleeve member of the footwear-protecting sock is coupled to the hollow body portion. The protective sleeve member includes the opening at a first end thereof adapted to surround and receive an upper portion of the user's footwear and elastic gripping members substantially surrounding the opening thereof to form the attachment mechanism of the protective sleeve and adapted to secure the sock and flexible, protective sleeve member to the upper portion of the footwear.

A second embodiment of the protective hosiery of the present invention includes a second opening at a second end of the main sleeve member with a second attachment mechanism surrounding the second end. The second embodiment of the present invention further includes a second protective sleeve member coupled to the hollow body portion with the second protective sleeve member having an opening at a first end thereof and an attachment mechanism surrounding the opening.

The protective hosiery of the present invention is particularly adapted for work boots, snow boots and with the installation of medical casts. The present invention includes a method of installing an intrusion-proof cast for setting a broken limb. The method includes the steps of a) inserting the limb into protective hosiery of the present invention;

b) securing the main sleeve member of the protective hosiery to the limb with the attachment mechanism of the main sleeve;

c) installing a hardened cast member over the hollow body portion of the main sleeve member;

d) overlapping one end of the cast member with the flexible, protective sleeve; and e) securing the protective sleeve member to the cast member with the attachment mechanism of the protective sleeve.

The present invention may be usefully applied in industrial or mechanical situations not involving clothing or human limbs but where it is desired to removably cover a gap between two surfaces, particularly surfaces of generally cylindrical shape, to prevent entry of air, water or debris therebetween.

These and other objects of the present invention will be clarified in the description of the preferred embodiments taken together with the attached figures wherein like reference numerals represent like elements throughout.

DESCRIPTION OF THE PREFERRED EMBODIMENTS

FIGS. 1–4 illustrate a footwear protecting sock 10 according to a first embodiment of the present invention. The footwear protecting sock 10 includes a flexible main sleeve member 12 and a flexible, protective sleeve member 14 coupled to the main sleeve member 12.

Figure 2:
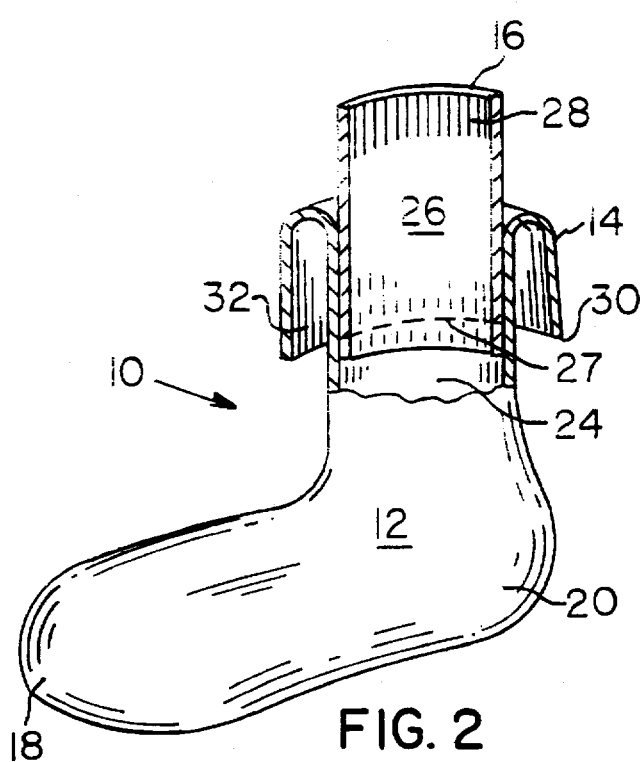
FIG. 2 is a perspective view, partially in section, of the protective sock illustrated in FIG. 1.
Figure 4:
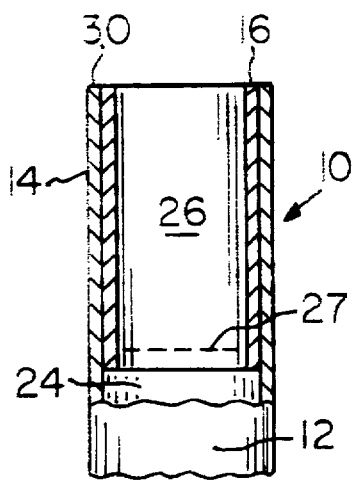
FIG. 4 is a section view of a portion of the protective sock illustrated in FIG. 3.

The main sleeve member 12 includes an opening 16 at a first end thereof which is adapted to receive a user's foot and leg therethrough. The flexible main sleeve member 12 additionally includes a hollow body portion which includes a toe-receiving portion 18, a heel-receiving portion 20 and a leg-receiving portion for receiving the ankle and calf of the leg, depending on the height of the main sleeve member 12. The hollow body portion is formed of a lower portion 24, which includes the toe-receiving portion 18, heel-receiving portion 20 and an upper portion 26 which is sewn to the lower portion 24 as best shown in FIGS. 2 and 4. This construction will minimize the seam 27 as viewed from the exterior of the sock 10 and provide a quick, easy procedure for producing the sock 10. Additionally, with this construction, the flexible, protective sleeve member 14 is formed integral with the lower portion 24 of the main sleeve member 12 in a conventional fashion as in ordinary sock construction.

Figure 1:
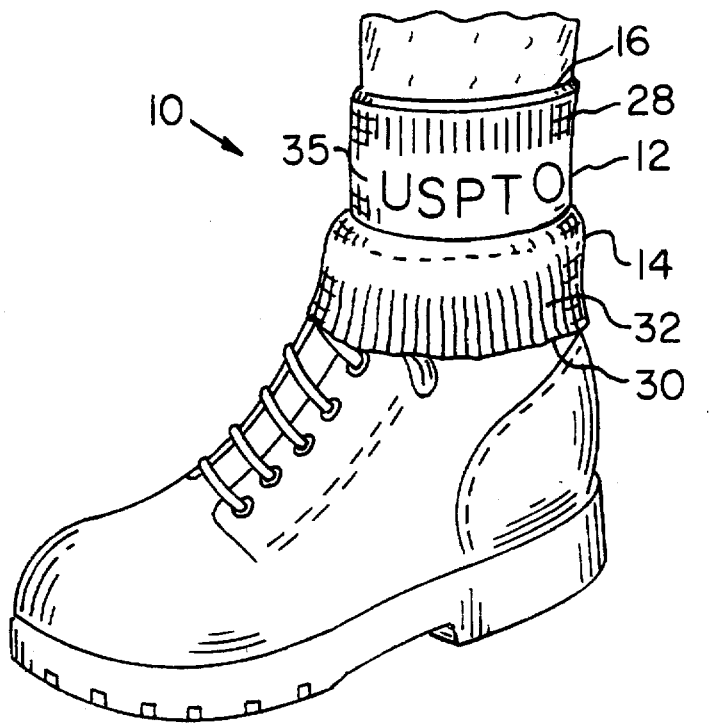
FIG. 1 is a perspective view of a footwear protective sock according to a first embodiment of the present invention.

Elastic gripping members 28 are provided in the upper portion 26 substantially surrounding the opening 16 and are adapted to secure the sock 10 to the leg of the user as illustrated in FIG. 1. The elastic gripping members 28 are formed in a conventional fashion such as elastic members sewn into the fabric of the sock 10.

The flexible, protective sleeve member 14 is coupled to the hollow body portion of the sleeve member 12 as discussed above. The protective sleeve member 14 includes an opening 30 at a first end thereof which is adapted to surround and receive an upper portion of the user's footwear as shown in FIG. 1. Elastic gripping members 32 are incorporated in the flexible, protective sleeve member 14 substantially surrounding the opening 30 and are adapted to secure the sock 10 to the upper portion of the footwear as shown in FIG. 1. The elastic gripping members 32 may be substantially the same as the elastic gripping members 28 discussed above and can be formed in a conventional fashion.

In operation, the sock 10 is placed on the foot of the user with the user's toes and heel received in the toe-receiving portion 18 and heel-receiving portion 20 in a conventional fashion by being inserted through the opening 16. The user's footwear is placed over the sock 10 and the protective sleeve member 14 is overlapped over the upper portion of the user's footwear, as shown in FIG. 1. Within the context of the present application, footwear should encompass any type of shoe, boot or cast as will be described hereinafter.

The footwear protecting sock 10 illustrated in FIGS. 1-4 of the present invention is particularly suited for use in the construction industry with construction work boots as described above. Consequently, it is anticipated that the protective sock 10 would be made out of a fabric material such as cotton or the like as is well known in the hosiery art. The sock 10 is also particularly relevant to snow boots as discussed above. Consequently, the fabric material for making the sock 10 may also be a waterproof material to assure that the user's foot is maintained in a dry condition.

Figure 3:
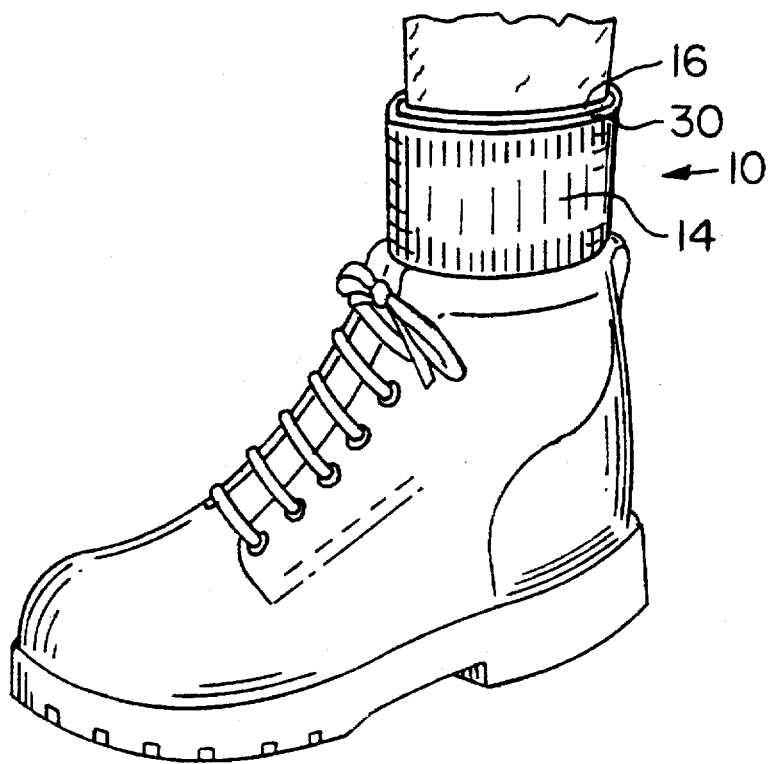
FIG. 3 is a perspective view of the protective sock illustrated in FIG. 1.

The sock 10 of the present invention additionally provides the ability to change the overall appearance of the sock 10. Specifically, sock 10 of the present invention may be worn as a conventional sock with the protective sleeve member 14 against the user's leg as shown in FIG. 3. The appearance of the sock 10 will be dictated by the exterior surface of the protective sleeve member 14. An alternative design can be presented by rolling the protective sleeve member 14 down over the top of the footwear, as illustrated in FIG. 1, in which event the interior surface of the protective sleeve member 14 and the exterior surface of the upper portion 26 would define the appearance of the sock 10. The exterior surface of the upper portion 26 and the interior surface of the protective sleeve member 14 may be formed of complementary designs, colors, or a logo 35 as shown in FIG. 1 and, importantly, this may differ significantly from the appearance presented on the exterior surface of the protective sleeve member 14. This configuration will allow the sock 10 of the present invention to present multiple versions of distinctly different appearances. This feature of the sock 10 of the present invention may be particularly well received by children.

When placing a limb in a cast, the area to be wrapped with a hardening cast is generally covered with a gauze-type material prior to placement of the cast so that the cast is not formed directly on the skin. The sock 10 of the present invention is particularly well suited for use in place of the gauze for a hardened cast on the foot, ankle or lower leg of the user. Where appropriate, the foot and leg can be placed into the sock 10 as described above. A hardening cast is installed over the hollow body portion of the sock 10. After the cast is set, the upper end of the cast would be overlapped with the flexible, protective sleeve member 14 and the protective sleeve member 14 secured to the cast through the resilient gripping members 32. The sock 10 of the present invention provides an intrusion-proof cast, preventing debris and other material from entering into the interior of the cast. This is particularly important as the cast stays on, and the muscle atrophies from lack of use, decreasing in size. The atrophy of the muscle will increase the gap between the edge of the cast member and the skin. The sock 10 of the present invention can maintain the cast in a sealed condition despite such muscle atrophy. Additionally the protective sleeve member 14 can easily be restored to a non-overlapped position to permit air to enter the gap when desired.

Figure 5:
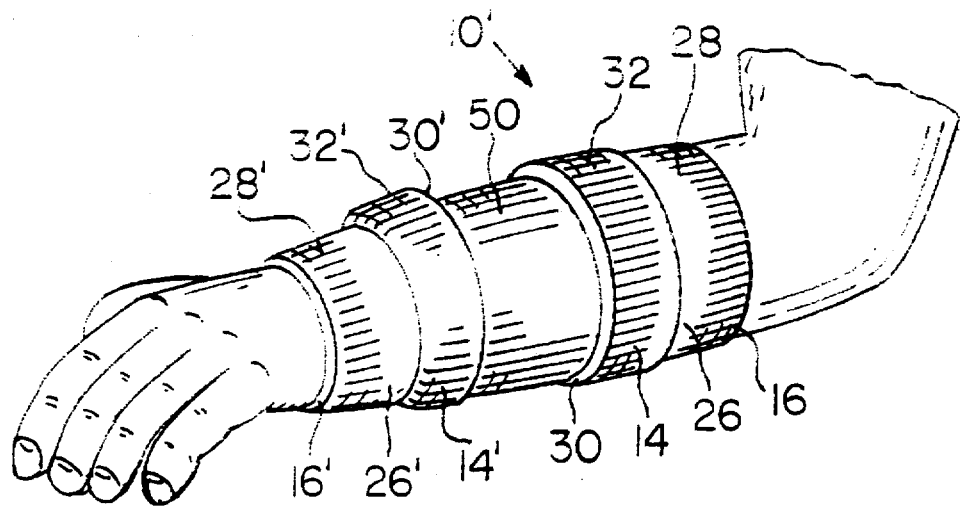
FIG. 5 is a perspective view of protective hosiery according to a second embodiment of the present invention.

FIG. 5 illustrates protective hosiery 10' according to a second embodiment of the present invention and is particularly adapted for installing an intrusion-proof cast 50 on an arm or upper leg of the user. The protective hosiery 10' is substantially the same as the sock 10 described above except that the second end thereof includes an opening 16' formed by an additional portion 26' with gripping members 28' therein. A second protective sleeve member 14' is attached at the second end with an opening 30' and resilient gripping members 32' provided therein substantially the same as the protective sleeve member 14, opening 30 and gripping members 32 described above. The protective hosiery 10' is adapted for use with a cast on the arms or upper legs of the user where the limb to be set is positioned all the way through the protective hosiery 10'. Both protective sleeve members 14 and 14' will be overlapped around one end of the cast member to protect both respective sides of the cast member as illustrated in FIG. 5.

It will be apparent to those of ordinary skill in the art that various changes may be made to the present invention without departing from the spirit and scope thereof. Consequently, the scope of the present invention is intended to be defined by the attached claims.

What is claimed is:

1. Protective hosiery comprising:
   a flexible main sleeve member having a hollow body portion, a first main sleeve member opening at a first end thereof, a second main sleeve member opening at a second end thereof, a first main sleeve member attachment means substantially surrounding said first main sleeve member opening, and a second main sleeve member attachment means substantially surrounding said second end;

a first flexible, protective sleeve member coupled to said hollow body portion of said main sleeve member, said first protective sleeve member having a first protective sleeve member opening at a first end thereof and a first protective sleeve member attachment means substantially surrounding said first protective sleeve member opening; and a second protective sleeve member coupled to said hollow body portion of said main sleeve member, said second protective sleeve member having a second protective sleeve member opening at a first end thereof and a second protective sleeve member attachment means substantially surrounding said second protective sleeve member opening.

2. The hosiery of claim 1 wherein each said attachment means includes resilient elements.

3. The hosiery of claim 2 wherein each said sleeve member is a fabric sleeve member.

4. The hosiery of claim 2 wherein said first protective sleeve member is integral with said main sleeve member.

5. The hosiery of claim 4 wherein said hollow body portion of said main sleeve member includes an upper portion sewn to a lower portion thereof to form said main sleeve member.

6. A method of installing an intrusion-resistant cast for setting a limb, said method comprising the steps of:

a) inserting the limb into protective hosiery, said protective hosiery including a flexible main sleeve member having a hollow body portion, a main sleeve member opening at a first end thereof, and a main sleeve attachment means substantially surrounding said main sleeve member opening, and at least one flexible, protective sleeve member coupled to said hollow body portion of said main sleeve member, said protective sleeve member having a protective sleeve member opening at a first end thereof and a protective sleeve attachment means substantially surrounding said protective sleeve member opening;

b) securing said main sleeve member to the limb with said main sleeve attachment means;

c) installing a hardened cast member over said hollow body portion;

d) overlapping one end of said cast member with said flexible, protective sleeve member; and e) securing said protective sleeve member to said cast member with said protective sleeve attachment means.

* * * * *